United States Patent [19]

Chavkin et al.

[11] 4,097,606

[45] Jun. 27, 1978

[54] APAP TABLET CONTAINING AN ALKALI METAL CARBOXYMETHYLATED STARCH AND PROCESSES FOR MANUFACTURING SAME

[75] Inventors: Leonard Chavkin, Mountainside; F. Henry Merkle, Scotch Plains, both of N.J.

[73] Assignee: Bristol-Myers Company, New York, N.Y.

[21] Appl. No.: 620,688

[22] Filed: Oct. 8, 1975

[51] Int. Cl.$^2$ .................. A61K 31/165; A61K 47/00
[52] U.S. Cl. .................................................. 424/324
[58] Field of Search ........................................ 424/324

[56] References Cited

U.S. PATENT DOCUMENTS

| | | | |
|---|---|---|---|
| 3,034,911 | 5/1962 | McKee et al. | 106/210 |
| 3,079,303 | 2/1963 | Raff et al. | 424/35 X |
| 3,266,992 | 8/1966 | De Jong | 424/280 X |
| 3,424,842 | 1/1969 | Nurnberg | 424/94 |
| 3,490,742 | 1/1970 | Nichols | 252/99 |
| 3,622,677 | 11/1971 | Short et al. | 424/361 |
| 3,632,778 | 1/1972 | Sheth et al. | 424/319 |
| 3,946,110 | 3/1976 | Hill | 424/230 |
| 4,013,785 | 3/1977 | Weintraub et al. | 424/23 |

FOREIGN PATENT DOCUMENTS 2,355,204  5/1974  Germany.

OTHER PUBLICATIONS

"Primojel" Edward Mendell Co. Inc. Tech. Bull., May 1972, An Evaluation of Carboxymethyl Starch as a Tablet Disintegrant, Nov. 1970, Determination of the Efficacy of Primojel as a Disintegrating Agent in Several Compressed Pharmaceutical Tablet Formulations (60 seconds disintegration-84% emcompress-10% APAP-5% Primojel).

Jaminet et al., Pharmaceutica Acta Helvetiae, 44:418-432 (1969).

Khan et al., J. Pharm. Pharmac. 23 Suppl. pp. 261S-262S (1971), An Evaluation of Five Commercially Available Tablet Disintegrants for Possible Use in Insoluble Direct Compression Systems.

Reier et al., Chem. Abstracts 64 #19327d (1966) of J. Pharm. Sci. 55(5): 510-514 (1966), "Micro-Crystalline Cellulose in Tableting".

Merck Index, 8th ed. (1968), p. 5, entry "Acetaminophen" APAP.

*Primary Examiner*—Shep K. Rose
*Attorney, Agent, or Firm*—Irving Holtzman; David J. Mugford; George A. Mentis

[57] ABSTRACT

APAP tablet containing from about 190 to 1000 milligrams of APAP, from 25 to 100 milligrams of an alkali metal salt of a low substituted carboxymethyl starch such as sodium or potassium, and preferably sodium and, optionally, a non-toxic pharmaceutically acceptable binder in a quantity equal to or less than the amount of APAP in the tablet. Several methods are described for preparing these tablets.

25 Claims, No Drawings

APAP TABLET CONTAINING AN ALKALI METAL CARBOXYMETHYLATED STARCH AND PROCESSES FOR MANUFACTURING SAME

This invention relates to analgesic tablets containing N-acetyl-p-aminophenol (hereinafter referred to as APAP). More particularly, it concerns tablets of this character which have relatively high absorption rates for APAP as measured by the blood plasma level of APAP over time after ingestion of APAP tablets.

APAP has long been known in the pharmaceutical and medical arts to be useful as an analgesic and/or antipyretic agent and has found its way into several commercially available products including tablets. Subsequent to ingestion of APAP in tablet form, the rate of onset of the intended pharmacologic action may be slower than desired and also quite variable from subject-to-subject. Such slowness and variability apparently result form the fact that absorption of APAP from the gastrointestinal tract into the blood stream is inhibited as a consequence of the process usually used in making these tablets. It has also been suggested that ordinary tablets may yield poor or variable absorption of APAP because gastric emptying is insufficiently rapid.

It has now been found that APAP tablets having an improved absorption rate can be prepared if the tablets are formulated so that they have the following compositions:

(a) about 190 to about 1000 milligrams of APAP;

(b) about 25 to about 100 milligrams of an alkali metal salt, preferably sodium salt of carboxymethyl starch (hereinafter referred to as alkali metal or sodium CMS); and (c) a binder; wherein (d) the weight ratio of APAP to salt of CMS is in the range of from about 3:1 to 20:1; and wherein (e) the binder is present in an amount in the range of from zero to an amount that is no greater than about the quantity of APAP contained in the tablet and preferably in the range of from zero to an amount that is no greater than about one half of the APAP contained in the tablet. When the binder is present, it will ordinarily be present in the range of from about 150 to 500 milligrams. Although the invention is applicable to any alkali metal salt of said carboxymethyl starch for simplicity, it will be described in respect to sodium CMS.

In the preferred forms of this invention, the APAP will be present in the tablet in the range of between about 325 to about 500 milligrams and the sodium CMS in the range of between about 30 to 90 milligrams. Moreover, the preferred range of the ratio of APAP:-sodium CMS is from about 5:1 to 10:1. Optimum results are obtained with a ratio of about 5:1.

In the practice of the present invention, it is an advantage to use a low substituted sodium carboxymethylated starch i.e. a starch in which the degree with which the starch hydroxy groups are etherified with a sodium carboxymethyl group is low. A sodium CMS that is particularly suitable for the present purposes is one in which the degree of substitution is about 0.25 to 0.29.

A commercially available sodium CMS that is highly advantageous for the present purposes is marketed under the trade name PRIMOJEL. This is described as being represented by the following formula:

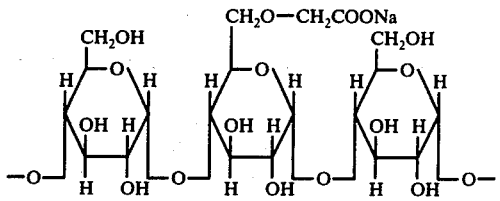

and having a M.W. of about 1,000,000. Other suitable commercially available sodium CMS products are PRIMOJEL L.V. and the National Starch Company sodium CMS No. 78–1702. The latter is prepared from potato starch.

The degree of substitution (DS) of PRIMOJEL is about 0.25, this meaning that per 100 glucose units, approximately 25 carboxy-methyl groups have been introduced. The glucopyranose units in starch are connected to each other by alpha-glucosidic linkages. It is a fine, white, flowable powder having a pH of 5.5 to 7.5 (in a 2% dispersion in distilled water) and an ash content of approximately 15% consisting of sodium chloride (approximately 5%) and sodium carbonate which is derived from the carboxyl groups present in PRIMOJEL. This product is further identified as giving a positive starch-iodine reaction, a blue coloring being achieved with a slightly acidified solution of iodinepotassium iodide. Furthermore, the sodium salt of the carboxyl groups demonstrates a specific absorption in the infra-red spectrum at 1600 cm$^{-1}$. The particle size analysis is given as follows:

All particles pass through a 125 micron sieve (115 mesh)

| | |
|---|---|
| 125 – 140 mesh | max. 4% |
| 140 – 200 mesh | max. 11% |
| 200 – 270 mesh | 18 – 42% |
| through 270 mesh | 45 – 75% |

There are several suitable processes for preparing the tablets of the present invention. In one procedure in which exceptionally good tablets are formed, the APAP and the sodium CMS, with or without binding agent, all in solid form and appropriate proportions, are first introduced into a blender or mixing machine. An anhydrous or substantially anhydrous granulating liquid is then introduced into the mixing machine. The quantity of this granulating liquid can vary somewhat. However, it will ordinarily be employed in the range of from about 15% to 50 % by weight based on the total weight of the mixture to be granulated. After thorough mixing of the granulating liquid with the powdered mix, the product is then preferably lightly screened and then dried. Any of the usual drying procedures may be employed e.g. air drying, fluid bed drying, pan drying or combinations thereof. The dried product is then screened to obtain a granulation suitable for tabletting. The tabletting aids such as the lubricants and/or flow promoting agents are then mixed with the granulated mix and the resulting product is then tabletted on a press such as a Stokes Rotary Press.

In practicing the aforesaid process, it has been found to be advantageous to use anhydrous or substantially anhydrous granulating liquids. These will usually take the form of anhydrous or substantially anhydrous organic solvents in which the APAP is at least somewhat soluble. A number of solvents are known in the prior art which would meet these criteria. By way of illustration, mention may be made of the anhydrous or substantially anhydrous lower monohydric alkyl alcohols having 1 to 6 carbon atoms (e.g. methanol, ethanol, propanol, isopropanol, butanol, isobutanol, n-pentanol (or its position isomers), hexanol (or its position isomers). As further illustration of the granulating liquids that are useful in this process, the following can be given: chloroform, methylene chloride alone or in combination with the aforesaid alcohols.

In a second process for preparing the present tablets, rather than using an anhydrous or substantially anhydrous granulating liquid as described above, an hydroalcoholic solvent containing as little as 20% by weight of an alkyl alcohol (e.g. containing 1 to 4 carbon atoms) may be employed. Satisfactory results are obtained when the hydroalcoholic solvent contains between about 20% and 50% by weight of the alcohol. The procedure is essentially the same as that described above in which an anhydrous or substantially anhydrous granulating fluid is employed. The only variation is that the hydroalcoholic liquid is used in place of the anhydrous or substantially anhydrous liquid.

In a third process for preparing the tablets of the present invention, no liquid granulating agent is employed at all. In such procedures, a dry blend is formed of APAP and sodium CMS with or without other ingredients. This is then pre-compacted using a suitable procedure (e.g. slugging, chilsonating). The aggregates formed in these pre-compacting processes are then reduced to a size suitable for tabletting and compressed into tablets.

Applicants' experience to date seems to indicate that improved absorption rates are not essentially or critically bound to the particular process employed in making the tablets. As will be made clearer from the discussion below, improved absorption rates have been demonstrated with tablets prepared by two entirely different types of procedures i.e. by the procedure that employs an anhydrous or substantially anhydrous granulating liquid and the procedure that employs no granulating liquid at all but a pre-compacting step.

In preparing tablets of the present invention, there may be incorporated in the composition prior to tabletting conventional tabletting aids or ingredients. Typical among these materials there may be mentioned: binders, disintegrants, lubricants, diluents, colors, etc. These are more specifically exemplified by the following:

binders: microcrystalline cellulose, lactose, sucrose;
disintegrants: corn starch, potato starch;
lubricants: magnesium stearate, talc, stearic acid;
diluents: lactose, sucrose;
flow aids: colloidal silicon dioxide (CAB-O-SIL M-5)

Among the binders that may be used in accordance with this invention, the present experience appears to indicate that microcrystalline cellulose offers some special advantage. Microcrystalline cellulose is marketed under the trade name AVICEL which is manufactured by the American Viscose Corp. The preparation of this material is described by Battista in Ind. Eng. Chem. 42, page 502–507 (1950) and in U.S. Pat. Nos. 2,978,446 and 3,141,875; all of which are incorporated herein by way of reference. This material is a non-fibrous powder having the following characteristics: Particle shape: rigid rod; Refractive index: 1.55; Bulk density: 18–19 lb/cubic foot; Practically insoluble, but dispersible in water; partially soluble with swelling in dilute alkali; practically insoluble in and resistant to dilute acid; practically insoluble and inert in organic acids. Chemically this cellulose has the same basic structure as conventional cellulose $(C_6H_{10}O_5)_n$. It is a polysaccharide with glucose units linked as in cellulose. Generally, these materials will have a so-called "level-off" D.P. (Degree of Polymerization) of from about 25 to 300 (See Battista article Page 503 for the method of measuring the degree of polymerization) and a particle size in the range of from 20 to 100 microns. The microcrystalline cellulose that may be used to the greatest advantage has a D.P. value (degree of polymerization) in the range of from about 210 to about 230.

It may sometimes be advantageous to also incorporate in these tablets other pharmaceutically active ingredients. By way of illustrating these active materials, the following may be mentioned: analgesics such as aspirin, propoxyphene; decongestants such as phenylpropanolamine (or the hydrochloride), phenylephrine (or the hydrochloride) or other pharmaceutically acceptable salts of these decongestants; antihistamines such as methapyrilene (or its hydrochloride), diphenhydramine (or its hydrochloride) (BENADRYL), chlorpheniramine (or its maleate) or other pharmaceutically acceptable salts, antacids such as calcium carbonate, magnesium hydroxide, aluminum hydroxide. However, in the preferred embodiments of this invention, the pharmacologically active material will consist essentially of APAP.

Tablets prepared in accordance with the present invention may vary with respect to the APAP content. This will depend upon the size of the tablet, the size of the dose to be administered at any one time and the number of tablets to be given at any one time. As used herein, the term unit dosage amount is used to describe the quantity of material in question that goes into a single tablet. This may comprise all or a portion of the dose of material to be administered at any one particular time. Ordinarily, the unit dosage amount of APAP contained in the tablets of the present invention will vary from about 190 milligrams to about 1000 milligrams and will preferably amount to about 325 or 500 milligrams of APAP. The sodium CMS in each unit dose will amount to from about 25 milligrams to 100 milligrams and preferably from about 30 milligrams to 90 milligrams.

Two studies were carried out to test the relative 60 minute bioavailability of Free APAP from tablets embodied in the present invention, as compared with a commercial APAP tablet. The commercial tablet is identified by the code BJ 9206 and has the following analysis:

| BJ 9206 | |
|---|---|
| Total weight | 460 mg |
| APAP | 325 mg |
| Cab-O-Sil | 1–2 mg |
| Avicel (+ small amount of starch) | Balance of tablet |

The tablets of the present invention that were used are identified by the codes CP 914-64 and CK 957-30A. These tablets have the same composition; however, tablets CP 914-64 were granulated with anhydrous isopropanol and compressed on a rotary press to a hardness of 10–11 SCU. Tablets CK 957-30A, on the other hand, were granulated with absolute ethanol and compressed on a single punch press to a hardness of about 6 SCU. (See Examples 2 and 3 below for composition and preparation of tablets coded CP 914-64 and CK 957-30A).

In Study I, 19 subjects were employed in a crossover study. Each fasted subject received 10 grains of APAP, either as two tablets of the commercial tablet BJ 9206 or two tablets of CK 957-30A of the present invention. The Free APAP plasma levels of each subject were determined by a modified Brodie Method at 10, 20, 40 and 60 minutes after ingestion and reported as micrograms per milliliter of blood plasma.

In Study II, 20 subjects were employed in a crossover study. Each fasted subject received 650 mg. of APAP, either as two commercial tablet BJ 9206 or two tablets CP 914-64 of this invention. The Free APAP plasma levels of each subject were also determined in these cases by the same method i.e. a modified Brodie Method at the same time intervals and reported in the same manner as in Study I.

The results of each of these studies are given in Table I below. In addition, the results obtained by statistically combining the results of Studies I and II are also given.

invention were both numerically and statistically superior to those obtained with the commercial APAP tablets. There is also recorded in the last column the "Average of Individual Peak Time". This is the average of time elapsed after ingestion of the respective tablets before the Free APAP plasma levels reached their peak in the individuals. It will be seen that in all cases, on the average, the peak level of Free APAP was reached in a shorter period of time in those subjects who took the tablets of the present invention, as compared with the commercial APAP tablet.

A further study (Study III) was conducted to compare the 60 minute bioavailability of Free APAP from tablets of the present invention prepared by two different procedures on the one hand with that of a commercial APAP tablet on the other hand. The commercial APAP product is the same one described above and identified by the code BJ 9206. The two products of the present invention that were tested in this study was the product coded CP 914-64 (see Example 2 below for formulation) and product coded No. 1144-06-14 (see Example 6 below for formulation).

TABLE I

COMPARISON OF AVERAGE FREE APAP PLASMA LEVELS
(mcg/ml)

|  |  | 10 Min. | 20 Min. | 40 Min. | 60 Min. | Average of Individual Peak Time (Minutes) |
|---|---|---|---|---|---|---|
| STUDY I | n = 19 |  |  |  |  |  |
| BJ 9206 |  | 3.08 | 6.94 | 7.85 | 6.78 | 42.6 |
| CK 957-30A |  | 6.31 | 8.75 | 8.57 | 8.07 | 36.3 |
| STUDY II | n = 20 |  |  |  |  |  |
| BJ 9206 |  | 1.41 | 4.61 | 8.06 | 8.46 | 46.8 |
| CP 914-64 |  | 3.62 | 7.68 | 10.27 | 9.25 | 36.0 |
| COMBINING STUDIES I & II | n = 39 |  |  |  |  |  |
| BJ 9206 |  | 2.22 | 5.74 | 7.96 | 7.64 | 44.8 |
| CK 957-30A |  | 4.93 | 8.20 | 9.44 | 8.67 | 36.2 |
| CP 914-64 |  |  |  |  |  |  |

Study I shows that at all time intervals, the Free APAP plasma levels obtained with the tablets of the present invention were numerically superior to those obtained with the commercial APAP tablet and that this superiority was also a statistical superiority at the 10 minute time interval. Study II also shows that at all time intervals the APAP plasma levels obtained with the tablets of the present invention were numerically superior to those obtained by the commercial APAP tablet and that this superiority was also a statistical superiority at the 10, 20 and 40 minute time intervals. The statistical combination of the results obtained from Studies I and II shows that at all time intervals the Free APAP plasma levels obtained with the tablets of the present A contemporaneous three-way cross-over study comparing the Free APAP plasma concentrations produced in 20 subjects of a blood panel was carried out. Each fasted subject received 650 mg. of APAP, either as two commercial APAP tablets (BJ 9206), two tablets in which APAP powder was granulated together with 55 mg. Primojel (CP 914-64), or two tablets which contain the identical ingredients as Formula CP 914-64 in which all the materials were dry blended, compressed into slugs, ground, passed through a 0.078 inch screen and tabletted (Code 1144-06-14). Free APAP plasma levels were determined by a modified Brodie Method.

The results of this study are summarized in Table II.

TABLE II

|  |  | BJ 9206 | No. 1144-06-14 | CP 916-64 |
|---|---|---|---|---|
| Free APAP, Average (Median) Plasma Concentration mcg/ml | 10 Min. | 2.35(1.00) | *6.85(7.65) | *6.95(4.65) |
|  | 20 Min. | 6.95(5.35) | *10.43(11.70) | *11.14(12.45) |
|  | 40 Min. | 9.26(9.50) | 10.24(10.20) | 11.60(11.85) |
|  | 60 Min. | 9.66(9.30) | 9.65(10.20) | 10.46(10.35) |
| Average of the Areas under the Individual Plasma Concentration Time Curves mcg/ml × hr (0–1 hr) |  | 6.82 | 8.77 | 9.55 |
| Peak of Average Plasma Concentrations Time Curve mcg/ml |  | 9.66 | 10.43 | 11.60 |
| Time of the Peak of the Average Plasma Concentration Time Curve (Minutes) |  | 60 | 20 | 40 |
| Average of the Individual Peak |  |  |  |  |

TABLE II-continued

|  | BJ 9206 | No. 1144-06-14 | CP 916-64 |
|---|---|---|---|
| Times (Minutes) | 41.5 | 30.0 | 31.0 |

*Significantly greater than BJ 9206 .05 level

The average data (see Table II and FIG. 1) shows that the relative 60 minute bioavailability of Free APAP obtained with Formula 1144-06-14 is not significantly different than that obtained from Formula CP 916-64, both of which are representative of the present invention. However, both are superior to Formula BJ 9206 i.e. the commercial APAP tablet.

The average Free APAP plasma concentrations obtained with Formula CP 916-64 are numerically greater than those from Formula BJ 9206 at all time intervals while those from Formula 1144-06-14 are numerically greater at the 10, 20 and 40 minute intervals. The drug level was higher in a significantly larger number of subjects (0.05 level) receiving Formula CP 916-64 or Formula 1144-06-14 than Formula BJ 9206 at the 10 and 20 minute sample periods.

The total 60 minute bioavailability as measured by the area under the 60 minute average Free APAP plasma drug curve is 6.82 mcg/ml × hr for BJ 9206 and 8.8 mcg/ml × hr for Formula 1144-06-14 and 9.5 mcg/ml × hr for Formula CP 916-64. Thus, Formula 1144-06-14 provided 128.6% and Formula CP 916-64 provided 140.0% of the drug supplied by BJ 9206. For Formula 1144-06-14 the average of the individual peak drug times, was 30.0 minutes and for Formula CP 916-64 the average was 31.0 minutes while for BJ 9206 (the commercial product) it was 41.5 minutes. This further demonstrates the noted more rapid absorption as a consequence of our invention.

The use of sodium CMS as a disintegrant to decrease the disintegration time and/or to increase the dissolution rate of certain materials has been suggested in the prior art. In this connection, attention is directed to Khan et al, "J. Pharm. Pharmac, 1971, 23, Suppl., 261S-262S and Jaminet et al, "Pharmaceutica Acta Helvetiae", 44, 418-432 (1969). These references, however, nowhere suggest the combination of APAP with sodium CMS. Moreover, these references nowhere suggest that the incorporation of the sodium CMS in the tablets would increase the absorption rate of the active materials contained in the tablets, much less that it would increase the absorption rate of APAP from a tablet containing soidum CMS.

Edward Mendell Co., Inc. in a trade bulletin carrying the date of November 1970 entitled "Determination of the Efficacy of Primojel as a Disintegrating Agent in Several Compressed Pharmaceutical Tablet Formulation" describes a 500 milligram tablet containing 10% APAP, 5% Primojel, 84% Emcompress (dicalcium phosphate dihydrate U.S.P.) and 1% magnesium stearate. This reference also does not disclose that the Primojel would be effective in increasing the rate of absorption of APAP from tablets containing the same. Furthermore, the amount of APAP contained in the tablet of this reference is obviously far lower than that contained in the tablets of the present invention. Moreover, the amount of binder of the Mendell tablet (i.e. Emcompress) is relatively far in excess of that contained in the instant tablets.

Rifat Parvez in a thesis submitted to Columbia University, College of Pharmaceutical Sciences in May 1972 entitled "A Low Substituted Carboxy-Methyl Starch as a Disintegrant in Compressed Tablets" also describes 500 milligram tablets containing 25% APAP, 67.5% of a binder (e.g. Lactose), 5% disintegrant (Primojel), 2% Acacia mucilage and 0.5% magnesium stearate. However, this reference likewise does not disclose that Primojel would be effective in increasing the rate of absorption of APAP from tablets containing the same. Moreover, like the Mendell tablet, the Parvez tablet contains the APAP in an amount that is far below that of the present invention (i.e. 125 milligrams as compared with at least 190 milligrams). Furthermore, like Mendell, the amount of binder in the Parvez tablet (i.e. lactose) is relatively far in excess of that contained in the tablets of this invention.

It may be further pointed out that the tablets described by Mendell and Parvez are not commercially feasible or consumer acceptable tablets. To make a tablet containing the usual amount of APAP, when it is the sole pharmacologically active agent (i.e. 325 milligrams), in the case of Parvez this would result in a tablet that would have a weight in excess of 1300 milligrams. Such a tablet would be too large for easy ingestion. Similarly, in the case of the Mendell tablet, this would weigh about 3200 milligrams which is well above what would be acceptable to the consumer.

It is now generally recognized that the overwhelming majority of drug substances ingested as solid dosage forms (tablets, capsules, etc.) must dissolve from the dosage form into the gastrointestinal fluids before transfer into the blood and to sites of action can take place. Mere disintegration or deaggregation of a solid into numerous smaller particles cannot assure an adequate or even significant degree of dissolution even though the deaggregation process provides a much greater surface area from which dissolution should occur. Dissolution rates, therefore, have become an increasingly important tool in formulating well absorbed products. However, as experience with dissolution rate studies has increased and become more sophisticated over the last fifteen years, it has been learned that in vitro dissolution tests offer only a tenuous guide for the proper formulation of the dosage form. There are numerous examples of product forms having dissolution rate superiority by a factor of 2 or 5 or 10 over other product forms but which show no enhancement in rate of absorption into the blood. Furthermore, an increasing amount of data is now available in which dosage forms, which show faster in vitro dissolution rates than other dosage forms, provide lower blood levels or decreased rates of absorption when compared with other dosage forms.

The following Examples are given to further illustrate the present invention. It is to be understood, however, that these are given only by way of illustration and this invention is not limited thereto.

The materials identified below used in the Examples or elsewhere have the following definitions:

Sodium CMS (Primojel) - This is the sodium salt of carboxymethyl starch having a degree of substitution of 0.025 and an average molecular weight of about 1,000,000.

Microcrystalline Cellulose (AVICEL PH-101) - This is cellulose in crystalline form having an average particle size of about 50 microns and an average degree of polymerization of about 220.

Colloidal Silicon Dioxide M-5 (CAB-O-SIL M5) - This is a fumed silicon dioxide manufactured by the Cabot Corporation produced by the hydrolysis of silicon tetrachloride at 1100° C. This has a surface area [$M^2$/gm (BET)] of 200 ± 25, a particle size of 0.012 microns and a density (lbs/cu ft) of 2.3 max.

National Starch Sodium CMS No. 78-1702 - Prepared from potato starch; DS about .25

Povidone (K-29-32) - Polyvinylpyrrolidone; medium M.W. 25,000.

PEG 6000 - Polyethylene glycol of formula H(OCH$_2$CH$_2$)$_n$OH where n has an average value of about 6000.

EXAMPLE 1

| CP 914-38B | |
|---|---|
| APAP | 324 mg. per tablet |
| Sodium CMS (PRIMOJEL) | 36 mg. per tablet |
| Microcrystalline Cellulose (AVICEL PH-101) | 160 mg. per tablet |
| Stearic acid, T.P. powder | 5 mg. per tablet |
| | 525 mg per tablet |

Dry blend the first three ingredients and granulate with anhydrous ethanol (250 ml. per 1000 tablets). Pass wet granulation through 18 mesh screen and dry in a fluid bed dryer without heat. Add and blend in the stearic acid, and compress to weight using 7/16 inch standard concave punches on a single-punch Manesty F-3 press.

EXAMPLE 2

| CP 914-64 | |
|---|---|
| APAP | 325 mg. per tablet |
| Sodium CMS (PRIMOJEL) | 55 mg. per tablet |
| Microcrystalline Cellulose (AVICEL PH-101) | 160 mg. per tablet |
| Stearic acid, T.P. powder | 5 mg. per tablet |
| Colloidal Silicon Dioxide M-5 | 0.5 mg. per tablet |
| | 545.5 mg. per tablet |

Dry blend the first three ingredients and granulate with anhydrous isopropanol (250 ml. per 1000 tablets). Pass wet granulation through a 12-mesh screen, spread on trays, and allow most of the alcohol to evaporate at room temperature. Complete the drying in a fluid bed dryer with low heat. Add and blend in the stearic acid and silicon dioxide, pass through 12-mesh screen, and compress to weight using 7/16 inch standard concave punches on a single-punch Manesty F-3 press.

EXAMPLE 3

| CP 957-30A | |
|---|---|
| APAP | 325 mg. per tablet |
| Sodium CMS (PRIMOJEL) | 55 mg. per tablet |
| Microcrystalline Cellulose (AVICEL PH-101) | 160 mg. per tablet |
| Stearic acid, T.P. powder | 5 mg. per tablet |
| Colloidal Silicon Dioxide M-5 | 0.5 mg. per tablet |
| | 545.5 mg. per tablet |

Procedure same as for Example 2 above, except that anhydrous ethanol used as the granulating liquid (250 ml. per 1000 tablets).

EXAMPLE 4

| CK 957-30B | |
|---|---|
| APAP | 325 mg. per tablet |
| Sodium CMS (PRIMOJEL) | 55 mg. per tablet |
| Microcrystalline Cellulose (AVICEL PH-101) | 160 mg. per tablet |
| Sodium Lauryl Sulfate, powder | 2 mg. per tablet |
| Stearic acid, T.P. powder | 5 mg. per tablet |
| Colloidal Silicon Dioxide M-5 | 0.5 mg. per tablet |
| | 547.5 mg. per tablet |

Dry blend the first four ingredients and granulate with anhydrous ethanol (250 ml. per 1000 tablets). Pass wet granulation through a 16-mesh screen and dry with the aid of a fluid bed dryer using mild heat (below 50° C). Add and blend in the stearic acid and silicon dioxide, and compress to weight using 7/16 inch standard concave punches on a single-punch Manesty F-3 press.

EXAMPLE 5

| CK 1014-5 | |
|---|---|
| APAP | 500 mg. per tablet |
| Sodium CMS (PRIMOJEL) | 75 mg. per tablet |
| Microcrystalline Cellulose (AVICEL PH-101) | 150 mg. per tablet |
| Stearic acid, T.P. powder | 3 mg. per tablet |
| | 728 mg. per tablet |

Dry blend the first three ingredients, and granulate with 20% isopropanol in water (365 ml. per 1000 tablets). Pass wet granulation through a 20-mesh screen, and dry with the aid of a fluid bed dryer using mild heat (below 50° C) to a moisture content of 3%. Add and blend in the stearic acid and compress to weight using ⅝ inch capsule-shaped punches on a Stokes Rotary Press.

EXAMPLE 6

| PP 1144-06-14 | |
|---|---|
| APAP | 325 mg. per tablet |
| Sodium CMS (PRIMOJEL) | 55 mg. per tablet |
| Microcrystalline Cellulose (AVICEL PH-101) | 160 mg. per tablet |
| Stearic acid, T.P. powder | 5 mg. per tablet |
| Colloidal Silicon Dioxide | 0.5 mg. per tablet |
| | 545.5 mg. per tablet |

Dry blend all ingredients and compress into slugs on a rotary press. Grind slugs through an oscillator with 0.078 inch opening screen, and recompress to weight using 7/16 inch standard concave punches on a Stokes Rotary Press.

EXAMPLE 7

| CS 184-7 | |
|---|---|
| APAP | 325 mg. per tablet |
| Microcrystalline Cellulose (AVICEL PH-101) | 160 mg. per tablet |
| Sodium CMS (PRIMOJEL) | 55 mg. per tablet |
| Stearic acid | 5 mg. per tablet |
| | 545 mg. per tablet |

Screen APAP to remove fines smaller than 100 mesh. Blend with other ingredients well and compress to weight directly on Manesty F-3 press using 7/16 inch SC punches.

EXAMPLE 8

| CK 1014-2 | |
|---|---|
| APAP | 500 mg. per tablet |
| Microcrystalline Cellulose (AVICEL PH-101) | 243 mg. per tablet |
| Sodium CMS (PRIMOJEL) | 75 mg. per tablet |
| Colloidal Silicon Dioxide M-5 | 2 mg. per tablet |
| Stearic acid | 5 mg. per tablet |
| | 825 mg. per tablet |

Blend all ingredients, pass through 20-mesh screen. Slug on single-punch press using 7/8 inch FFBE punches. Reduce slugs on oscillator using 4-mesh screen, then 10-mesh screen. Compress to weight on ¾ inch capsule-shaped punch.

EXAMPLE 9

| CK 1014-8 | |
|---|---|
| APAP | 500 mg. per tablet |
| Microcrystalline Cellulose (AVICEL PH-101) | 227 mg. per tablet |
| Sodium CMS (PRIMOJEL) | 84.6 mg. per tablet |
| Colloidal Silicon Dioxide M-5 | 3.8 mg. per tablet |
| Stearic acid | 3.8 mg. per tablet |
| Water | 19.2 mg. per tablet |
| | 838.4 mg. per tablet |

Blend first four ingredients, spray with the water and pass through chilsonator to compact. Pass compacted cake through oscillator (0.078 inch screen), blend in stearic acid and compress to weight on ¾ inch capsule-shaped punch.

EXAMPLE 10

| CK 1014-1A | |
|---|---|
| APAP | 500 mg. per tablet |
| Sodium CMS (PRIMOJEL) | 75 mg. per tablet |
| Microcrystalline Cellulose (AVICEL PH-101) | 150 mg. per tablet |
| | 725 mg. per tablet |

Blend all three ingredients, granulate with 50% isopropanol (340 ml. per 1000 tablets). Pass wet granulation through 12-mesh screen, dry in fluid bed dryer, no heat. Pass dry granulation through 20-mesh screen, and compress to weight using ¾ inch capsule-shaped punch.

EXAMPLE 11

| CK 1014-6 | |
|---|---|
| APAP | 500 mg. per tablet |
| Microcrystalline Cellulose (AVICEL PH-101) | 150 mg. per tablet |
| Sodium CMS (PRIMOJEL) | 75 mg. per tablet |
| Stearic acid | 3 mg. per tablet |
| | 728 mg. per tablet |

Blend first three ingredients, granulate with 10% isopropanol (375 ml. per 1000 tablets). Pass wet granulation through 12-mesh screen, dry in fluid bed dryer, no heat. Pass dry granulation through 20-mesh screen, add and blend in the stearic acid, and compress to weight using ¾ inch capsule-shaped punch.

EXAMPLE 12

| CP 914-79 | |
|---|---|
| APAP | 500 mg. per tablet |
| Microcrystalline Cellulose (AVICEL PH-101) | 100 mg. per tablet |
| Starch, corn | 75 mg. per tablet |
| Sodium Lauryl Sulfate | 1.5 mg. per tablet |
| Povidone K-29-32 | 7.5 mg. per tablet |
| Sodium CMS (PRIMOJEL) | 29 mg. per tablet |
| Polyethylene Glycol 6000 | 2 mg. per tablet |
| | 715.0 mg. per tablet |

Dissolve the Povidone and the sodium lauryl sulfate in water (300 ml. per 1000 tablets), and use to wet granulate a mixture of the first three ingredients. Dry in fluid bed dryer with mild heat to a moisture content of about 4%. Add the sodium CMS and PEG 6000, blend well and compress to weight on ¾ inch capsule-shaped punches.

EXAMPLE 13

| CP 914-33 | |
|---|---|
| APAP | 324 mg. per tablet |
| Sodium CMS (PRIMOJEL) | 36 mg. per tablet |
| Microcrystalline Cellulose (AVICEL PH-101) | 160 mg. per tablet |
| Stearic acid | 5 mg. per tablet |
| | 525 mg. per tablet |

Co-evaporate the first two ingredients with methanol. Blend with other ingredients and compress to weight using 7/16 inch SC punches.

EXAMPLE 14

| CP 914-48 | |
|---|---|
| APAP | 324 mg. per tablet |
| Calcium carbonate | 81 mg. per tablet |
| Sodium CMS (PRIMOJEL) | 25 mg. per tablet |
| Microcrystalline Cellulose (AVICEL PH-101) | 165 mg. per tablet |
| Stearic acid | 5 mg. per tablet |
| | 600 mg. per tablet |

Co-evaporate the first two ingredients from metanol. Blend in rest of ingredients, and compress to weight using 7/16 inch SC punches.

EXAMPLE 15

| PP 1144D-04-11 | |
|---|---|
| APAP | 325.00 mg. per tablet |
| Sodium CMS (PRIMOJEL) | 55.00 mg. per tablet |
| Microcrystalline Cellulose (AVICEL PH-101) | 147.50 mg. per tablet |
| Colloidal Silicon Dioxide M-5 | 2.50 mg. per tablet |
| Deionized water | 12.50 mg. per tablet |
| Stearic acid | 2.50 mg. per tablet |
| | 545.00 mg. per tablet |

Blend APAP, Primojel, Microcrystalline cellulose and Colloidal Silicon Dioxide M-5 in a Ribbon Blender or any other suitable mixer. Spray the deionized water into the mixer. Pass the mixture through a Tornado Mill with an A-251-761-2 opening screen at high speed. Compact the above mixture through a compactor (Chilsonator). Oscillate the compacted material through a 0.078 opening 8 mesh screen. Mix the granulation with stearic acid powder in a double cone type mixer. Compress on a single layer tablet press to a thickness of 0.210 inch ± 0.005 inch.

| Ingredient | Milligrams per tablet | | |
|---|---|---|---|
| | Ex. 16A CP 1024-1A | Ex. 16B CP 1024-1B | Ex. 16C CP 1024-1C |
| APAP | 325.00 | 325.00 | 325.00 |
| Microcrystalline Cellulose (AVICEL PH-101) | 159.00 | 159.00 | 159.00 |
| Stearic acid T. P. powder Emersol 6332 | 5.00 | 5.00 | 5.00 |
| PRIMOJEL | 36.00 | — | — |
| PRIMOJEL LV | — | 36.00 | — |
| National Starch Sodium CMS No. 78-1702 | — | — | 36.00 |
| Colloidal Silicon Dioxide M-5 | 0.50 | 0.50 | 0.50 |
| | 525.50 | 525.50 | 525.50 |

In each of the above Examples 16A–16C the ingredients were mixed by dry blending. The mixture was then slugged and the slugs were screened through a number 10 mesh screen by hand. The material resulting from this screening was then compressed into tablets.

The following Examples are given in tabular form. The quality of each ingredient is given in terms of mg. per tablet. The process code number appearing in this Table refers to the following numbered procedures:

1. All ingredients mixed well, and fed to tablet press directly without any intermediate preparative steps.
2. All ingredients mixed well, pre-compressed usually with large size punch and heavy pressure, reduced to compressible particles by use of a mill, and then compressed again into tablets.
3. All ingredients mixed well, pre-compated on a chilsonator, (passes between compacting rollers with a waffle-like design), reduced to compressible particles by use of a mill, and then compressed again to proper size and weight tablets.
4. All ingredients except lubricant and sometimes the disintegrant, are mixed well, wetted with anhydrous ethanol until a damp mass has formed. This is dried by spreading on trays or by use of a fluid bed dryer, and the dried granules are passed through a sizing screen or a mill. The remaining ingredients are mixed in and the mixture is then fed to a tablet press.
5. Same as procedure 4 using isopropanol.
6. Same as procedure 4 using 50% isopropanol.
7. Same as procedure 4 using 20% isopropanol.
8. Same as procedure 4 using 10% isopropanol.
9. Same as procedure 4 using water.
10. APAP is dissolved in methanol, colloidal silicon dioxide added and dispersed, and the methanol evaporated to recrystallize the APAP in the presence of the colloidal silicon dioxide.
11. APAP is dissolved in methanol, sodium CMS added and dispersed, and the methanol evaporated.
12. APAP is dissolved in methanol, $CaCO_3$ added and dispersed, and the methanol evaporated.
13. APAP and colloidal silicon dioxide prepared as an aqueous slurry, fed to a spray drier, and collected as a co-dried mixture.

When two numbers appear as an entry under the "Process Code" of Table III, this indicates that the tablets of this example were prepared using a combination of procedures. The order in which the two numbers appear in the entry indicates the order in which the procedures were carried out. Thus, for example, in Example 17 the tablets were prepared by first following the procedure 10 described above and then completing the process with the procedure 1 also described above.

What is claimed is:

1. As an article of manufacture, a tablet having a relatively high absorption rate for N-acetyl-p-aminophenol as measured by the blood plasma level of N-acetyl-p-aminophenol over time after ingestion comprising:
    (a) from about 190 to 1000 milligrams of N-acetyl-p-aminophenol;
    (b) from about 30 to 90 milligrams of a low substituted alkali metal carboxymethyl starch; and
    (c) a non-toxic, pharmaceutically acceptable binder; the ratio of N-acetyl-p-aminophenol to sodium alkali metal carboxymethyl starch, on a weight basis, being in the range of from about 5:1 to 10:1; the quantity of binder present being in the range of from 0 to an amount no greater than the amount of N-acetyl-p-aminophenol contained in the tablet.
2. A tablet according to claim 1 also including a lubricant.
3. A tablet according to claim 1 also containing up to 4 milligrams of a flow aid.
4. A tablet according to claim 2 also including up to 4 milligrams of a flow aid.
5. A tablet according to claim 1 also including a material selected from the class consisting of disintegrants, diluents, sodium lauryl sulfate, calcium carbonate, polyvinylpyrrolidone, polyethylene glycol and mixtures thereof.
6. A tablet according to claim 2 also including a material selected from the class consisting of disintegrants, diluents, sodium lauryl sulfate, calcium carbonate, polyvinylpyrrolidone, polyethylene glycol and mixtures thereof.
7. A tablet according to claim 3 also including a material selected from the class consisting of disintegrants, diluents, sodium lauryl sulfate, calcium carbonate, polyvinylpyrrolidone, polyethylene glycol and mixtures thereof.
8. A tablet according to claim 4 also including a material selected from the class consisting of disintegrants, diluents, sodium lauryl sulfate, calcium carbonate, polyvinylpyrrolidone, polyethylene glycol and mixtures thereof.
9. A tablet according to claim 1 in which the binder is present in an amount in the range of from about 150 to 500 milligrams.
10. A tablet according to claim 9 in which the binder is a microcrystalline cellulose.
11. A tablet according to claim 10 also including a lubricant.
12. A tablet according to claim 10 also including up to about 4 milligrams of a flow aid.
13. A tablet according to claim 11 also including up to about 4 milligrams of a flow aid.
14. A tablet according to claim 9 also including a material selected from the class consisting of disintegrants, diluents, sodium lauryl sulfate, calcium carbonate, polyvinylpyrrolidone, polyethylene glycol and mixtures thereof.
15. A tablet according to claim 10 also including a material selected from the class consisting of disintegrants, diluents, sodium lauryl sulfate, calcium carbonate, polyvinylpyrrolidone, polyethylene glycol and mixtures thereof.

16. A tablet according to claim 11 also including a material selected from the class consisting of disintegrants, diluents, sodium lauryl sulfate, calcium carbonate, polyvinylpyrrolidone, polyethylene glycol and mixtures thereof.

17. A tablet according to claim 12 also including a material selected from the class consisting of disintegrants, diluents, sodium lauryl sulfate, calcium carbonate, polyvinylpyrrolidone, polyethylene glycol and mixtures thereof.

18. A tablet according to claim 13 also including a material selected from the class consisting of disintegrants, diluents, sodium lauryl sulfate, calcium carbonate, polyvinylpyrrolidone, polyethylene glycol and mixtures thereof.

19. As an article of manufacture, a tablet having a relatively high absorption rate for N-acetyl-p-aminophenol as measured by the blood plasma level of N-acetyl-p-aminophenol over time after ingestion consisting essentially of:
(a) from about 325 to 500 milligrams of N-acetyl-p-aminophenol;
(b) from about 30 to 90 milligrams of a low substituted sodium carboxymethyl starch; and
(c) from about 150 to 500 milligrams of microcrystalline cellulose;
the ratio of N-acetyl-p-aminophenol to said sodium carboxymethyl starch being in the range of from about 5:1 to 10:1.

20. A tablet according to claim 19 including stearic acid as a lubricant.

21. A tablet according to claim 19 including up to 4 milligrams of colloidal silicon dioxide as a flow aid.

22. A tablet according to claim 21 in which the tablet contains about 0.5 milligrams of colloidal silicon dioxide.

23. A tablet according to claim 21 also including sodium lauryl sulfate.

24. A tablet according to claim 20 also including calcium carbonate.

25. A tablet according to claim 10 in which the degree of substitution of said low substituted alkali metal carboxymethyl starch is in the range of from 25 to 29 alkali metal carboxymethyl groups per 100 glucose units of said starch and said microcrystalline cellulose has a degree of polymerization in the range of from 210 to 230.

* * * * *

UNITED STATES PATENT AND TRADEMARK OFFICE
CERTIFICATE OF CORRECTION

PATENT NO. : 4,097,606
DATED : June 27, 1978
INVENTOR(S) : LEONARD CHAVKIN ET AL It is certified that error appears in the above-identified patent and that said Letters Patent are hereby corrected as shown below:

Column 7, line 48, change "soidum" to read -- sodium --
Column 9, Example 3, change "CP 957-30A" to

-- CK 957-30A --

Signed and Sealed this

Third Day of April 1979

[SEAL]

Attest:

RUTH C. MASON
Attesting Officer

DONALD W. BANNER
Commissioner of Patents and Trademarks